(12) United States Patent
Clark et al.

(10) Patent No.: US 7,192,913 B2
(45) Date of Patent: Mar. 20, 2007

(54) ENHANCING THE FRAGRANCE OF AN ARTICLE

(75) Inventors: David G. Clark, Gainesville, FL (US); Kenichi Shibuya, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/779,508

(22) Filed: Feb. 13, 2004

(65) Prior Publication Data

US 2004/0229770 A1 Nov. 18, 2004

Related U.S. Application Data

(60) Provisional application No. 60/514,795, filed on Oct. 27, 2003, provisional application No. 60/447,062, filed on Feb. 13, 2003.

(51) Int. Cl.
*A61Q 13/00* (2006.01)
(52) U.S. Cl. ........................................................ 512/1
(58) Field of Classification Search .................... 512/1, 512/5; 73/23.34
See application file for complete search history.

(56) References Cited

U.S. PATENT DOCUMENTS 4,868,339 A * 9/1989 Christenson et al. ....... 568/376
5,263,359 A * 11/1993 Mookherjee et al. ...... 73/23.34
5,269,169 A * 12/1993 Trenkle et al. ............. 73/23.34
5,321,005 A * 6/1994 Mookherjee et al. .......... 512/5
5,321,006 A * 6/1994 Mookherjee et al. .......... 512/5
5,355,718 A * 10/1994 Mookherjee et al. ...... 73/23.34
5,367,899 A * 11/1994 Mookherjee et al. ...... 73/23.34
5,369,978 A * 12/1994 Mookherjee et al. ...... 73/23.34

* cited by examiner

*Primary Examiner*—Monique T. Cole
(74) *Attorney, Agent, or Firm*—Akerman Senterfitt; Nicholas A. Zachariades

(57) ABSTRACT

A composition having a fragrance that substantially mimics a fragrance of a plant is made by (a) identifying a plurality of different chemical entities emitted from a plant, wherein the plurality of different chemical entities combine to form the fragrance of the plant; (b) determining a concentration of the plurality of different chemical entities emitted from the plant, the plurality of different chemical entities including at least a first chemical entity and a second chemical entity, the first and second chemical entities having different chemical structures; (c) providing a stock of the first chemical entity and a stock of the second chemical entity; and (d) mixing together aliquots of the stock of the first chemical entity and the stock of the second chemical entity to form a mixture wherein a ratio of the concentration of the first chemical entity to second chemical entity is substantially the same as that emitted from the plant. The composition may be applied to an article such as a flower with little or no scent to enhance the articles fragrance.

3 Claims, No Drawings

ENHANCING THE FRAGRANCE OF AN ARTICLE

CROSS REFERENCE TO RELATED APPLICATION

This application claims the priority of U.S. provisional patent application No. 60/447,062, filed Feb. 13, 2003 and U.S. provisional patent application No. 60/514,795, filed Oct. 27, 2003.

STATEMENT AS TO FEDERALLY SPONSORED RESEARCH

Not applicable.

FIELD OF THE INVENTION

The invention relates to the fields of fragrances and flowers. More particularly, the invention relates to compositions and methods for enhancing the fragrance of an article.

BACKGROUND OF THE INVENTION

Plant breeding has led to flowers with bigger, longer-lasting blooms. Unfortunately, this breeding process has also led to flowers that have lost all or much of their scents.

SUMMARY OF THE INVENTION

The invention relates to compositions and methods for enhancing the scent of a article (e.g., cut flowers) by contacting the article with one or more chemical formulations that have a selected fragrance. For example, a composition that mimics the natural scent of a flower is prepared by mixing together stock chemicals in a ratio that is similar to that emitted from the flower. Applying this composition to a flower that has lost all or much of its scent through breeding can restore the lost or diminished scent to produce a more commercially desirable product.

The compositions of the invention may be formulated in liquid form and sprayed directly on cut flowers. They might also be added to vase solutions or embedded into floral arrangement hardware. As one example, for roses that do not emit a "rose" scent, to enhance their aesthetic appeal and therefore commercial value, a florist or consumer might spray the roses with a composition that mimics a natural rose scent.

The chemical makeup of the fragrant compositions of the invention are based on type and amount of scent-imparting chemicals that are emitted by a particular plant. For example, to devise a formulation that has the fragrance of a particular flower, the identity and relative concentration of the chemicals emitted from the flower may be determined using conventional chemical analysis. As one example, a gas flowed over a flower may be analyzed by gas chromatography (GC) to characterize the identity and concentration of chemicals emitted by the flower.

Using the methods of the present invention, compositions that substantially mimic the fragrance of a flower may be made from stock chemicals using the GC data as a guide. Although the exact formula generated from GC analysis might be used, other formulas that are similar to the exact formula might also be used. Beneficial formulas may be selected empirically, e.g., using a test panel. For example, a formulation that may be used to impart a "rose" odor to a flower (e.g., a hybrid rose that lacks or has only minimal fragrance) includes a mixture of 2-phenylethanol and beta-ionone. A formulation that may be used to impart a "petunia" odor includes a mixture of benzaldehyde, phenylacetaldehyde, methyl benzoate, 2-phenylethanol, caryophyllene, and benzyl benzoate.

Accordingly, the present invention features a method for producing a composition having a fragrance that mimics or substantially mimics that of a plant. The method includes the steps of: (a) identifying a plurality of different chemical entities emitted from a plant, wherein the plurality of different chemical entities combine to form the fragrance of the plant; (b) determining a concentration of the plurality of different chemical entities emitted from the plant, the plurality of different chemical entities including at least a first chemical entity and a second chemical entity, the first and second chemical entities having different chemical structures; (c) providing a stock of the first chemical entity and a stock of the second chemical entity; and (d) mixing together aliquots of the stock of the first chemical entity and the stock of the second chemical entity to form a mixture wherein a ratio of the concentration of the first chemical entity to second chemical entity is substantially the same as that emitted from the plant. More than two chemical entities may be needed, based upon the number of chemical entities identified, e.g. 3, 4 or more as necessary.

The plant may be selected from a variety of different plants including, but not limited to, rose, petunia, lilac, lavender, gardenia, orchid, snapdragon, cyclamen, lily, hyacinth, carnation, citronellia, mint, lemon, lime, orange, or pineapple. The first or second chemical entity may be a compound selected from those presented in Table 1 (below).

An exemplary composition having a fragrance that mimics that of a rose includes 2-phenylethanol and beta-ionone, e.g., at a molar ratio of about 2200:1. One that has a fragrance that mimics that of petunia, includes benzaldehyde, phenylacetaldehyde, methyl benzoate, 2-phenylethanol, caryophyllene, and benzyl benzoate.

The composition of the invention may also include a diluent such as water, hydroxypropyl beta-cyclodextrin (HP-BCD) and/or glycerol. It can also be encapsulated.

In yet another aspect, the invention features a method for enhancing the fragrance of an article. The method includes the step of: contacting the article with a composition having a scent that substantially mimics a natural fragrance of a plant.

Unless otherwise defined, all technical terms used herein have the same meaning as commonly understood by one of ordinary skill in the art to which this invention belongs. Although methods and materials similar or equivalent to those described herein may be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

DETAILED DESCRIPTION OF THE INVENTION

The present invention is more particularly described in the following description and examples that are intended to be illustrative only since numerous modifications and variations therein will be apparent to those skilled in the art. As used in the specification and in the claims, the singular form "a," "an," and "the" may include plural referents unless the context clearly dictates otherwise. The term "comprising" may include the embodiments "consisting of" and "consisting essentially of." By the phrase "a fragrance that substantially mimics a fragrance of a plant" or a like phrase is meant that the fragrance can be identified as originating from the plant by at least 50% of persons experienced in formulating fragrances. When referring to a concentration, "about" and "substantially the same" mean within 50% of the stated concentration. For example, the about 1 g/ml includes any concentration within the range of 0.5 to 1.5 g/ml.

The invention provides a composition for enhancing the fragrance of a plant or article, a plant or article treated with the composition, and methods of making and using such a composition.

Fragrant Compositions

Any composition having a fragrance that may be imparted on a plant or other article might be used in the invention. Those that mimic a naturally occurring scent or those that do not resemble a scent found in nature might be used. For applications that involve imparting a the odor of a first plant (flower) on another plant, compositions having a fragrance that mimics that of the first plant may be used. For example, a composition having a fragrance that mimics that of a plant includes a mixture of different molecules (e.g., 3, 4, 5, 6, 7, 8, 9, 10 or more different molecules) that are naturally emitted from the plant or that have an odor that resembles a molecule that contributes to the scent of a plant. Several scent-imparting molecules have been discovered to be emitted by plants including those presented in Table 1 below.

TABLE 1

Acetaldehyde; Ethanol; Acetic aldehyde;
Acetic acid; Ethanoic acid;
Acetoin; 3-Hydroxy-2-butanone;
Acetone; 2-Propanone; Propan-2-one; Dimethyl ketone;
Acetophenone; Methyl phenyl ketone;
Acetylpyrazine; 2-Acetylpyrazine;
Acetylpyridine; 2-Acetylpyridine;
Acetylpyrrole; 2-Acetylpyrrole; Methyl pyrrolyl ketone;
Acetylthiazole; 2-Acetylthiazole;
Allyl sulfide; Diallyl sulfide;
Ambrox ®; (+)-Ambrox isomer;
Ambrox ®; (−)-Ambrox isomer; Ambroxan;
Ambrox ®; DL-Ambrox isomer; Synambran;
Amyl alcohol; 1-Pentanol; Pentyl alcohol;
Amyl butyrate; n-Pentyl butanoate; Amyl butanoate;
Anisole; Methoxybenzene;
Benzaldehyde;
Benzenethiol; Thiophenol; Phenyl mercaptan;
Benzothiazole;
Benzyl alcohol;
Bornyl acetate;
Butanethiol; 1-Butanethiol;
Butanone; 2-Butanone; Methyl ethyl ketone;
Butyl acetate; n-Butyl acetate;
Butyl alcohol; Butanol; 1-Butanol; n-Butanol;
Butyl butyrate; Butyl butanoate;
Butyl hexanoate; Butyl caproate;
Butyl isobutyrate; n-Butyl 2-methylpropanoate;
Butyl methylbutyrate; n-Butyl 2-methylbutyrate;
Butyl propionate; n-Butyl propanoate;
Butylamine; 1-Aminobutane;
Butyraldehyde; Butanal; n-Butanal;
Butyric acid; n-Butanoic acid;
Carvone; (−)-carvone
Caryophyllene; beta-Caryophyllene;
Citral; Geranial isomer
Citral; Neral isomer
Citronellol; (+)-Citronellol isomer
Cresol; 2-Methylphenol; o-Cresol;

TABLE 1-continued

Cresol; 3-Methylphenol; m-Cresol;
Cresol; 4-methylphenol; p-Cresol;
Cyclocitral; beta-Cyclocitral isomer
Damascenone; beta- Damascenone;
Damascone; alpha- Damascone;
Damascone; (+)-alpha-Damascone isomer;
Damascone; (−)-alpha-Damascone isomer;
Decadienal; trans,trans-2,4-Decadienal;
Decalactone; gamma-Decalactone; 4-Decanolide;
Decalactone; delta-Decalactone; 5-Decanolide;
Decanal; Aldehyde C-10; Decyl aldehyde;
Decanoic acid; Capric acid;
Decenal; 2-Decenal; (E)-2-Decenal;
Diacetyl; 2,3-dioxobutane;
Dimethoxyphenol; 2,6-Dimethoxyphenol; Syringol;
Dimethyl disulfide; Methyl disulfide;
Dimethyl trisulfide; Methyl trisulfide;
3,4-Dimethyl-1,2-cyclopentanedione;
3,5-Dimethyl-1,2-cyclopentanedione;
2,5-Dimethyl-4-methoxy-3(2H)-furanone
Dimethylpyrazine; 2,3-Dimethylpyrazine;
Dimethylpyrazine; 2,5-Dimethylpyrazine;
Dimethylpyrazine; 2,6-Dimethylpyrazine;
Dimethylthiazole; 4,5-Dimethylthiazole;
Dimethyltrithiolane; 3,5-Dimethyl-1,2,4-trithiolane,
Dodecalactone; gamma-Dodecalactone; 4-Dodecanolide;
Dodecalactone; delta-Dodecalactone; 5-Dodecanolide;
Dodecanal; Lauric aldehyde; Aldehyde C-12; Dodecyl aldehyde;
Dodecanoic acid, Lauric acid;
Ethoxymethylpyrazine; 2-Ethoxy-3-methylpyrazine;
Ethyl acetate;
Ethyl acetoacetate; Acetoacetic acid, ethyl ester;
Ethyl acrylate;
Ethyl alcohol;
Ethyl benzoate;
Ethyl butyrate; Ethyl butanoate;
Ethyl cinnamate;
Ethyl heptanoate;
Ethyl hexanoate; Ethyl caproate;
Ethyl isobutyrate; Ethyl 2-methylpropanoate;
Ethyl lactate;
Ethyl methylbutyrate; Ethyl 2-methylbutyrate;
Ethyl 3-methylthiopropionate;
Ethyl palmitate; Ethyl hexadecanoate; Ethyl cetylate;
Ethyl phenylacetate;
Ethyl propionate; Ethyl propanoate;
Ethyl valerate; Ethyl pentanoate;
Ethyl vanillin; 3-Ethoxy-4-hydroxybenzaldehyde; Ethavan;
2-Ethyl-3,5-dimethylpyrazine;
2-Ethyl-3,6-dimethylpyrazine;
Ethyldimethylpyrazine; 3-Ethyl-2,6-dimethylpyrazine;
Ethylguaiacol; 4-Ethylguaiacol; 4-Ethyl-2-methoxyphenol;
Ethylhexanol; 2-Ethyl-1-hexanol; 2-Ethylhexan-1-ol;
Ethylhydroxymethylfuranone; 2-Ethyl-4-hydroxy-5-methyl-3(2H)furanone;
Ethyl methoxypyrazine; 2-Ethyl-3-methoxypyrazine;
Ethyl methylpyrazine; 2-Ethyl-5-methylpyrazine;
Ethyl methylpyrazine; 3-Fthyl-2-methylpyrazine;
Ethyl methylpyridine; 5-Ethyl-2-methylpyridine;
Ethylpyrazine; 2-Ethylpyrazine;
Eucalyptol; Cineole; 1,8-Cineole; 1,8-epoxy-p-menthane;
Eugenol; 4-Allyl-2-methoxyphenol;
Eugenyl methyl ether; Methyl eugenol; Methyl eugenol ether;
Farnesol;
Formic acid;
Furfural;
Furfuryl alcohol;
Furfuryl mercaptan;
Furyl methyl ketone; 2-Furyl methyl ketone; 2-Acetylfuran;
Geraniol; trans-3,7- Dimethyl-2,7-octadien-ol;
Geranyl acetate;
Geranyl acetone; 6,10-Dimethyl-5,9-undecadien-2-one;
Geranyl isobutyrate; Geranyl 2-methylpropanoate;
Geranyl propionate; Geranyl propanoate;
Glycerol; Glycerin;
Glycine; Aminoacetic acid;
Guaiacol; o-Methoxyphenol; o-Hydroxyanisole,
Heptalactone; gamma-Heptalactone; 4-heptanolide;
Heptanal; Aldehyde C-7; Heptaldehyde; Heptyl aldehyde;
Heptanoic acid;

TABLE 1-continued

Heptanone; 2-Heptanone; Methyl amyl ketone;
Heptenal, 4-Heptenal (cis and trans);
Heptenal; trans-2-Heptenal;
Heptenal; (E)-4-Heptenal; trans-4-Heptenal;
Heptenal; (Z)-4-Heptenal; cis-4-Heptenal;
Heptenone; 3-Hepten-2-one; (E)-3-Hepten-2-one
Heptyl alcohol; 1-Heptanol; n-Heptanol; Alcohol C-7;
Heptyl isobutyrate; Heptyl 2-methylpropanoate;
Hexadienal; (E,E)-2,4-Hexadienal; trans,trans-2,4-Hexadienal;
Hexalactone; gamma-Hexalactone; 4-Hexanolide; Hexan-4-olide;
Hexanal; Aldehyde C-6; Caproic aldehyde;
Hexanoic acid; Caproic acid;
Hexanol; 1-Hexanol; Hexyl alcohol; Caproic alcohol; Alcohol C-6;
Hexenal; 2-hexenal; Hex-2-enal; (E)-2-hexenal;
Hexenal; cis-3-Hexenal; (Z)-3-hexenal;
Hexenol; 3-Hexen-1-ol; cis-3-Hexenol;(Z)-3-Hexenol;
Hexyl acetate;
Hexyl butyrate; Hexyl butanoate;
Hexyl isobutyrate; Hexyl 2-methylpropanoate;
Hexyl methylbutanoate; Hexyl 2-methylbutanoate;
Hexyl propionate; Hexyl propanoate;
Hydroxydecadienoic acid lactone; 6-Pentyl-alpha-pyrone,
Hydroxydihydrotheaspirane; 6-Hydroxydihydrotheaspirane;
Indole;
Ionone; alpha-Ionone;
Ionone; beta-Ionone;
Isoamyl acetate; 3-Methylbutyl acetate;
Isoamyl alcohol, 3-Methyl-1-butanol; Isopentyl alcohol;
Isobutyl acetate;
Isobutyl alcohol; 2-Methyl-1-propanol;
Isobutyl isobutyrate; 2-Methylpropyl 2-methylpropanoate;
Isobutylmethoxypyrazine; 2-Isobutyl-3-methoxypyrazine;
Isobutylmethylpyrazine; 2-Isobutyl-3-methylpyrazine;
Isobutylthiazole; 2-Isobutylthiazole;
Isobutyraldehyde; 2-Methylpropanal;
Isobutyric acid; 2-Methylpropanoic acid;
Isovaleric acid; 3-Methylbutanoic acid;
Jasmine lactone; Dec-7-en-5-olide;
Limonene; d-Limonene;
Linalool;
Maltol; Veltol; Corps praline;
5-Ethyl-3-hydroxy-4-methyl-2(5H)-furanone; Maple furanone;
Menthenethiol; 1-p-Menthene-8-thiol;
Menthone; p-Menthan-3-one;
2-Methoxy-3-isopropylpyrazine;
2-Methoxy-5-isopropylpyrazine;
Methoxymethylphenol; 2-Methoxy-4-methylphenol; Creosol;
2-Methoxy-3-sec-butylpyrazine;
2-,5 or 6-Methoxy-3-methylpyrazine;
2-Methoxy-3-methylpyrazine;
5-Methoxy-2-methylpyrazine;
Methoxypyrazine; 2-Methoxypyrazine;
Methoxyvinylphenol; 2-Methoxy-4-vinylphenol; 4-Vinylguaiacol;
Methyl butyrate; Methyl butanoate;
Methyl 2-furylmethyl disulfide;
Methyl heptanoate;
Methyl hexanoate, Methyl caproate;
Methyl isobutyrate; Methyl 2-methyl propanoate;
Methyl mercaptan;
Methyl methylbutyrate; Methyl 2-methylbutyrate;
Methyl 3-methylthiopropionate;
Methyl octanoate; Methyl caprylate;
Methyl 1-propenyl disulfide;
Methyl salicylate;
Methyl sulfide; Dimethyl sulfide; Methylthiomethane;
Methyl valerate; Methyl pentanoate;
4-Methylacetophenone; p-Methylacetophenone;
Methylbutyl acetate, 2-Methylbutyl acetate;
Methylbutyraldehyde; 2-Methylbutyraldehyde;
Methylbutyraldehyde; 3-Methylbutyraldehyde; Isovaleraldehyde;
Methylbutyric acid; 2-Methylbutyric acid;
Methylcyclopentenolone; Cyclotene; Ketonarome; Corylone; MCP;
2-Methyl-3-(furfurylthio)pyrazine
2-Methyl-5-(furfurylthio)pyrazine
Methyl heptadienone; 6-Methyl-3,5-heptadien-2-one;
Methylheptenol; 6-Methyl-5-hepten-2-ol;
Methylheptenone; 6-Methyl-5-hepten-2-one;
2-Methyl-4-propyl-1,3-oxathiane;
(+)-cis-2-Methyl-4-propyl-1,3-oxathiane;
(−)-cis-2-Methyl-4-propyl-1,3-oxathiane;
Methylpyrazine, 2-Methylpyrazine;
4-Methyl-5-thiazoleethanol; Sulfurol;
Methylthioacetaldehyde; 2-Methylthioacetaldehyde;
Methylthiomethylpyrazine (mixture of isomers);
2-Methylthio-3-methylpyrazine;
5-Methylthio-2-methylpyrazine;
Methylthiophencarboxaldehyde; 2-Formyl-5-methylthiophene;
Methylthiopropanal; 3-(Methylthio)-propanal; Methional;
Myrcene;
Myristaldehyde; Tetradecanal; Aldehyde C-14 (Myristic);
Myristic acid; Tetradecanoic acid;
Nerol;
Nonadienal; (E,Z)-2,6-Nonadienal; trans,cis-2,6-Nonadienal;
Nonadienal; (E,E)-2,4-Nonadienal; trans,trans-2,4-Nonadienal;
Nonanal; Nonyl aldehyde; Aldehyde C-9;
Nonanoic acid;
Nonanol; 1-Nonanol; Nonyl alcohol; Alcohol C-9;
Nonanone; 2-Nonanone; Methyl heptyl ketone;
Nonenal; 2-Nonenal;
Nonenal; cis-6-Nonenal;
Nootkatone; (+)-Nootkatone (the natural isomer)
Nootkatone; (−)-Nootkatone (the unnatural isomer)
Octalactone; delta-Octalactone; 5-Octanolide;
Octalactone; gamma-Octalactone; 4-octanolide,
Octanal; Caprylic aldehyde; Aldehyde C-8;
Octanoic acid; Caprylic acid;
Octanol; 1-Octanol; Octyl alcohol,- Alcohol C-8;
Octanone; 2-Octanone;
Octanone; 3-Octanone;
Octenal; 2-Octenal;
Octenol; 1-Octen-3-ol;
Octenone; 1-Octen-3-one;
Octyl acetate;
Octyl isobutyrate; Octyl 2-methylpropanoate;
Palmitic acid; Hexadecanoic acid;
Pentadecalactone; omega-Pentadecalactone; 15-Pentadecanolide;
Pentanone; 2-Pentanone;
Pentenal; 2-Pentenal;
Pentenol, 1-Penten-3-ol;
Pentenone, 1-Penten-3-one; Ethyl vinyl ketone;
Pentenone, 3-Penten-2-one;
Pentylfuran; 2-Pentylfuran;
Pentylpyridine; 2-Pentylpyridine,
Phenethyl alcohol; 2-Phenethyl alcohol;
Phenol;
Phenylacetaldehyde;
Phenylacetic acid;
Pinene; alpha-Pinene;
Pinene; beta-Pinene;
Piperidine;
Piperonal; Heliotropine;
Propanethiol; 1-Propanethiol; n-Propyl mercaptan;
Propanol; 1-Propanol; Propyl alcohol;
Propenyl propyl disulfide; Propyl propenyl disulfide;
Propenylguaethol; 2-Ethoxy-5-propenylphenol;
Propionaldehyde; Propanal;
Propionic acid; Propanoic acid;
Propyl butyrate; Propyl butanoate;
Propyl propionate; Propyl propanoate;
Pyrazinyl methyl sulfide; 2-(Methylthiomethyl)-pyrazine;
Pyridine;
Pyrrole;
Pyrrolidine;
Quinoline;
Raspberry Ketone; 4-(p-Hydroxyphenyl)-2-butanone; Oxanone,
Rose oxide; 4-Methyl-2-(2-methylpropen-1-yl)-tetrahydropyran;
Sinensal; alpha-Sinensal;
Sotolon; Caramel furanone;
Stearic acid; Octadecanoic acid;
Strawberry furanone; 4,5-Dimethyl-3-hydroxy-2(5H)-furanone;
Styrene; Vinylbenzene;
Terpineol; alpha-Terpineol; p-Menth-1-en-8-ol;
Terpinolene; p-Menth-1,4(8)-diene;
Tetramethylpyrazine, 2,3,5,6-Tetramethylpyrazine;
Thiamine hydrochloride; (value for thiamine pure)
Thymol, 5-Methyl-2-isopropylphenol;
Trimethylamine;
2,2,6-Trimethylcyclohexanone, TABLE 1-continued Trimethyloxazoline; 2,4,5-Trimethyl-3-oxazoline;
Trimethyl pyrazine; 2,3,5-Trimethylpyrazine,
Trimethylthiazole; 2,4,5-Trimethylthiazole;
Undecalactone; delta-Undecalactone; 5-Undecanolide;
Undecanal; Aldehyde C-11 (undecylic);
Undecanoic acid; Undecylic acid;
Unclecanone; 2-Undecanone; Methyl nonyl ketone;
Valeraldehyde; Pentanal;
Valeric acid; Pentanoic acid;
Vanillin, 4-Hydroxy-3-methoxybenzaldehyde;
Vinylphenol; 4-Vinylphenol;

To make a composition having a fragrance that substantially mimics that of a plant, two or more of these scent-imparting molecules are mixed together in the same or similar molar ratio as is naturally emitted from the plant. Suitable molar ratios of the molecules may be determined by conventional analytical techniques including, but not limited to gas chromatography or mass spectrometry.

In addition to the mixture of scent-imparting molecules, the composition of the invention might also include other substances such as diluents (e.g., water, alcohol, sugar molecules, HPBCD (e.g., 5, 10, 15, 20%), and dimethyl-eta-cyclodextrin (DMCD)), colorants, preservatives, fixatives, and combinations thereof.

Making Fragrant Compositions

The invention further provides a method from making a composition having a fragrance that mimics that of a plant. In overview, the method includes the steps of: (a) determining the identity and concentration of at least two (e.g., 3, 4, 5, 6, 7, 8, 9, 10 or more) different chemical entities (i.e., molecules differing in chemical structure or formula) emitted from the plant; (b) providing stocks of the different chemical entities identified; and (c) mixing together aliquots of the stocks of the different chemical entities to form a mixture wherein the ratio of the concentration of the different chemical entities in the mixture is the same or about the same (e.g., by molar concentration 75, 80, 85, 90, 91, 92, 93, 94, 95, 96, 97, 98, 99, or 100% identical to) as that emitted from the plant.

The plant may be selected from a variety of different plants including, but not limited to, rose, petunia, lilac, lavender, gardenia, orchid, snapdragon, cyclamen, lily, hyacinth, carnation, citronellia, mint, lemon, lime, orange, or pineapple. The step of determining the identity and concentration of at least two different chemical entities may be performed by analyzing what molecules are emitted from the plant. For example, a fluid (e.g., a gas such as air or nitrogen) may be flowed over a plant placed in a container. The molecules in the fluid flowed over the plant are then analyzed for the presence and concentration of chemical entities. The analysis may be performed by conventional methods such as gas chromatography or mass spectrometry.

Once the different chemical entities have been identified, stocks of such chemicals may be made using synthetic techniques or may be obtained commercially. These stocks may be purified stocks. For example, a number of scent-imparting molecules have been identified. These include those listed in Table 1. Stock solutions of each of these may be obtained commercially, e.g., from Sigma-Aldrich or Acros Organics.

Aliquots of the stocks of the different chemical entities are then mixed together to form a mixture wherein the ratio of the concentration of the different chemical entities in the mixture is the same or substantially the same as that emitted from the plant. As such, this final fragrance composition substantially mimics the fragrance of the selected plant. The data obtained from the analysis of the chemical entities emitted from a plant may then be used to estimate the molar concentrations of each component of the mixture to generate the selected scent. Slight adjustments to each of the components may also be made to fine tune the scent. In alternative embodiments, a test panel may be used to empirically identify those fragrant compositions that do or do not substantially mimic the natural fragrance of the plant.

Article Treated With A Fragrant Composition

The present invention also provides an article treated with a fragrant composition of the invention. An article treated with a fragrant composition may be made by simply applying the composition on the article. For example, a fragrant composition of the invention be poured on or sprayed on the article or the article be immersed in the composition. Material making up the article might also be impregnated with the composition. To prevent or reduce evaporation of the composition from article the article might be covered with a gas impermeable material (e.g., a plastic sheet) that may be removed to release the fragrance of the composition.

Examples of articles to which the composition may be applied include almost any solid or liquid. In select embodiments, the articles are those that are generally associated with plants or flowers, e.g., plants, fresh flowers, dried flowers, artificial flowers, vases, planters and other flower arrangement paraphernalia. In one embodiment of the present invention, a flower, such as a rose, that has little natural fragrance is treated with a composition that mimics the natural fragrance of that flower (a rose in the example). Other articles may include, but are not limited to, paper products, such as stationary, linens, and potpourri.

The article may be treated using any known means for applying a composition to an article. In select embodiments, the fragrant composition is in the form of a liquid and the composition is sprayed onto the article. In alternative embodiments, the article may be directly contacted with the fragrant composition liquids, such as by dipping, immersing, or otherwise contacting the article with the liquid. In yet another alternative embodiment, the fragrant composition may be added to water and then added to the plant. In still another alternative embodiment, the fragrant composition may be added to water that is contained within the vessel holding the plant or flower. In still other alternative embodiments, the fragrant composition may be in the form of a solid or semi-solid, such as a gel or paste, and then applied to the article. In yet another alternative embodiment, the fragrant composition may be in the form of a solid tablet that may dissolve in water or another liquid.

The amount of the fragrant composition to be applied may vary as selected depending on various factors including, but not limited to, the strength of the fragrance to be emitted, the size of the article to be treated, and the concentration of the fragrant composition.

The present invention will now be further described through examples. It is to be understood that these examples are non-limiting and are presented to provide a better understanding of various embodiments of the present invention.

EXAMPLES

Example 1

Compositions for Imparting a "Rose" Fragrance

|  |  | (v/v) |
|---|---|---|
| Example 1A | | |
| 2-phenylethanol | $1.6 \times 10^{-2}$ M | $2.0 \times 10^{-1}$ % |
| beta-ionone | $7.4 \times 10^{-6}$ M | $1.4 \times 10^{-4}$ % |
| Example 1B | | |
| 2-phenylethanol | $1.2 \times 10^{-1}$ M | 1.5% |
| beta-ionone | $5.7 \times 10^{-5}$ M | $1.1 \times 10^{-3}$ % |
| Example 1C | | |
| 2-phenylethanol | $6.1 \times 10^{-2}$ M | $7.5 \times 10^{-1}$ % |
| beta-ionone | $5.7 \times 10^{-5}$ M | $1.1 \times 10^{-3}$ % |
| beta-damascone | $3.5 \times 10^{-5}$ M | $6.7 \times 10^{-4}$ % |
| Example 1D | | |
| 2-phenylethanol | $6.1 \times 10^{-2}$ M | $7.5 \times 10^{-1}$ % |
| beta-ionone | $5.7 \times 10^{-5}$ M | $1.1 \times 10^{-3}$ % |
| eugenol | $6.1 \times 10^{-7}$ M | $1.0 \times 10^{-5}$ % |

Example 2

Composition for Imparting a "Petunia" Fragrance

| | | |
|---|---|---|
| Benzaldehyde | $1.4 \times 10^{-5}$ M | $1.5 \times 10^{-4}$%(v/v) |
| phenylacetaldehyde | $3.5 \times 10^{-6}$ M | $4.2 \times 10^{-5}$% |
| Methyl Benzoate | $3.0 \times 10^{-5}$ M | $4.1 \times 10^{-4}$% |
| 2-phenylethanol | $7.3 \times 10^{-7}$ M | $8.9 \times 10^{-6}$% |
| caryophyllene | $4.3 \times 10^{-7}$ M | $9.5 \times 10^{-6}$% |
| benzyl benzoate | $4.2 \times 10^{-7}$ M | $8.8 \times 10^{-6}$% |

Example 3

Panel Testing

In this panel, 30 of 60 participants chose the sample flower that was different from the other two given in the triangle test. The panelists were able to detect a significant difference between the fragrance of the treated flowers and the fragrance of the non-treated flowers at a probability of <1%. Overall, the participants commented that the treated flowers smelled "sweeter" or "stronger" than non-treated control flowers and many commented positively on the fragrance of the treated flowers.

Example 4

Volatile Collection and Analysis

Floral volatiles were collected from excised flowers. Three flowers were collected per treatment and each time-point was repeated 3 times. Volatiles were collected for one hour according to collection protocol described by Schmelz et al (Planta 214: 171–179, 2001). Identification of each of the floral volatiles was verified by GC-MS (Id).

Although the illustrative embodiments of the present disclosure have been described herein with reference to the accompanying drawings and examples, it is to be understood that the disclosure is not limited to those precise embodiments, and various other changes and modifications may be affected therein by one skilled in the art without departing from the scope of spirit of the disclosure. All such changes and modifications are intended to be included within the scope of the disclosure as defined by the appended claims.

The invention claimed is:

1. A composition for enhancing the fragrance of a plant, the composition comprising at least a first chemical entity and a second chemical entity, the first and second chemical entities having different chemical structures; wherein the ratio of the concentration of the first chemical entity to the second chemical entity is substantially the same as that emitted from the plant and, wherein the composition has a fragrance that substantially mimics a fragrance of a rose and comprises 2-phenylethanol and beta-ionone, wherein 2-phenylethanol is the first chemical entity and beta-ionone is the second chemical entity.

2. The composition of claim 1, wherein the 2-phenylethanol and beta-ionone are present at a molar ratio of about 2200:1.

3. A composition having a fragrance that substantially mimics a fragrance of a petunia, wherein the composition comprises benzaldehyde, phenylacetaldehyde, methyl benzoate. 2-phenylethanol, caryophyllene, and benzyl benzoate.

* * * * *